United States Patent [19]

Dougherty

[11] 4,391,590
[45] Jul. 5, 1983

[54] CARTRIDGE FOR VISCOUS MATERIAL

[75] Inventor: Emery W. Dougherty, York, Pa.

[73] Assignee: Dentsply Research & Development Corp., Milford, Del.

[21] Appl. No.: 344,255

[22] Filed: Jan. 29, 1982

Related U.S. Application Data

[63] Continuation-in-part of Ser. No. 252,558, Apr. 9, 1981, Pat. No. 4,330,280.

[51] Int. Cl.³ .............................................. A61C 5/04
[52] U.S. Cl. ...................................................... 433/90
[58] Field of Search ............................. 433/90, 89, 80; 222/386

[56] References Cited

U.S. PATENT DOCUMENTS

| | | | |
|---|---|---|---|
| 2,505,028 | 4/1950 | Boeger | 433/90 |
| 2,847,009 | 8/1958 | Blease | 222/386 |
| 3,164,303 | 1/1965 | Trautmann | 222/386 |
| 4,295,828 | 10/1981 | Rudler | 433/90 |

*Primary Examiner*—Robert Peshock
*Attorney, Agent, or Firm*—C. Hercus Just

[57] ABSTRACT

A capsule-like cartridge comprising a cylindrical body of uniform diameter open at one end and provided with an annular flange surrounding the open end, the other end being closed by an integral hemi-spherical end of the same radius as said body and provided with an angularly extending discharge nipple communicating with the interior of the hemi-spherical end and body. After the body is loaded with a precisely measured quantity of material, the open end is closed by a plug slidably movable along said body when one end is engaged by a plunger of no greater diameter than said plug and the opposite end being complementary in shape to the hemi-spherical end of the body, whereby the plunger is capable of discharging the entire measured amount of material in the body except the scintilla thereof lodged in the nipple. The body and plug are molded from opaque material impervious to the passage of light and the tip of the nipple is closed by a cap which may be color-coded to indicate various facts as kind of material, weight or quantity, or otherwise.

2 Claims, 9 Drawing Figures

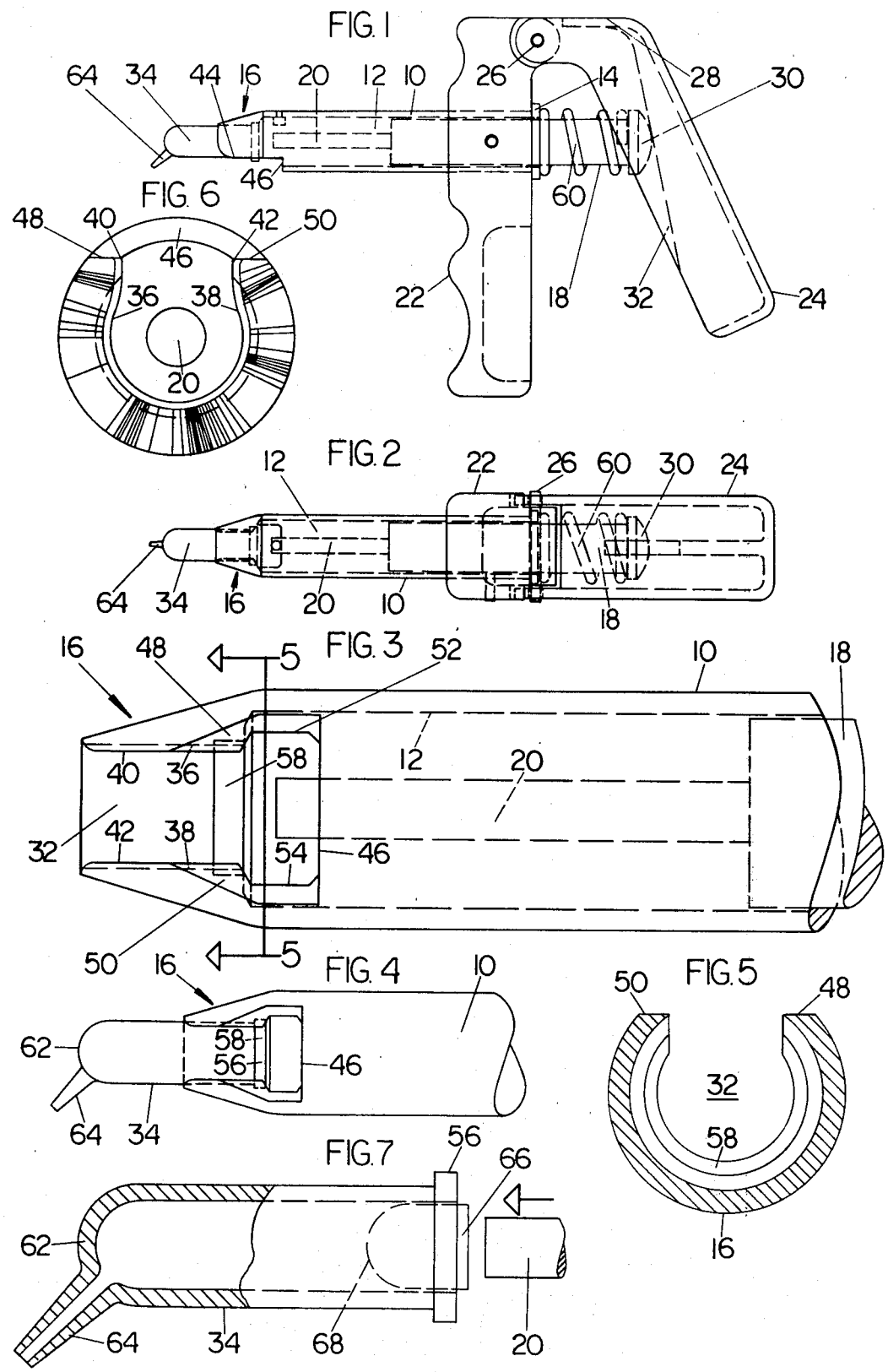

CARTRIDGE FOR VISCOUS MATERIAL

REFERENCE TO RELATED APPLICATION

This application is a continuation-in-part of application Ser. No. 252,558, filed Apr. 9, 1981 now U.S. Pat. No. 4,330,280 issued May 18, 1982, and entitled "Ejector Holder for Capsule-like Cartridges".

BACKGROUND OF THE INVENTION

In recent years it has become popular to package various types of material, especially medicinal or quasi-medicinal types in sealed cartridges, insertable in a suitable type of holder and/or ejector device, for purposes of preserving purity of the medicament and the like, insuring a patient of accurately measured quantities, as well as minimizing effort now required in introducing bulk amounts of material into a syringe and ejecting measured quantities thereof, for example. Various previous efforts in this direction are illustrated and described in various prior U.S. patents, particularly U.S. Pat. No. 3,581,399 to Dragan, dated June 1, 1971, in which a typical example of loaded cartridge is illustrated in conjunction with one type of holder and discharge device.

Other efforts have been made to produce similar devices, one of these comprising the subject matter of prior U.S. Pat. No. 3,900,954, also to Dragan, dated Aug. 26, 1975, and comprising a simpler version than in Dragan's patent, U.S. Pat. No. 3,581,399.

It has been found in the operation of the Dragan devices, particularly relative to the curved discharge end of the capsule or cartridges that there have been occasions when the leading end of the ejecting plunger or the piston within the cartridge pushed through the wall adjacent the outer end of the cartridge. Particularly for purposes of obviating this difficulty and also for providing an improved cartridge not subject to the difficulties of Dragan's cartridges and which is free of such difficulties, the present invention has been devised and details thereof are set forth hereinbelow.

Further, certain additional constructions in cartridges of the type described above are disclosed in prior U.S. Pat. No. 2,505,028 to Boeger, Dated Apr. 25, 1950.

SUMMARY OF THE INVENTION

It is among the principal objects of the present invention to provide an improved cartridge having a cylindrical elongated body open at one end and provided with a circular flange exteriorly of the open end and the opposite end of the cartridge being hemi-spherical and includes an angularly extending discharge nipple having a relatively small diameter elongated opening, said cartridge readily being rotatable about its axis when mounted within the barrel in order to direct the discharge at any angle desired by the operator, the cartridge being of uniform diameter exteriorly, as well as interiorly, and also including a piston having sidewalls closely complementary to the inner walls of the body and inserted into the open end thereof to form a closure, and also being formed on the inner end of the piston in hemi-spherical configuration and complementary to the interior surface of the closed end of the body of the cartridge, thereby eliminating any possibility of the piston rupturing the closed end of the cartridge and also insuring maximum delivery of material from the cartridge when the piston is fully inserted therein.

It is another object of the invention to form such improved cartridge by molding the body and piston from plastic material, such material optionally being opaque in color to permit loading the same with a light-sensitive material and storage thereof.

A further object of the invention is to provide the cartridge with a cap for the end of the discharge nipple which, in addition to sealing the nipple, affords the distinct additional advantage of permitting the cap to be color-coded to designate various facts such as type of material, quantity thereof, shade or color of the material, and otherwise.

Details of the foregoing objects and of the invention, as well as other objects thereof, are set forth in the following specification and illustrated in the accompanying drawing comprising a part thereof.

BRIEF DESCRIPTION OF THE DRAWING

FIG. 1 is a side elevation of an ejector holder for supporting a capsule-like cartridge which includes the principles of the present invention.

FIG. 2 is a top plan view of the holder and cartridge shown in FIG. 1.

FIG. 3 is a fragmentary enlarged bottom plan view of the forward end of the barrel of the ejector holder shown in FIGS. 1 and 2.

FIG. 4 is a fragmentary bottom plan view of the ejector holder similar to FIG. 3, but on a smaller scale, and illustrating a cartridge supported in the forward end of the barrel.

FIG. 5 is a vertical sectional view of the forward end portion of the barrel of the ejector holder shown in FIG. 3, as seen on the line 5—5 thereof.

FIG. 6 is a front end view of the forward end of the barrel shown in FIGS. 1–4.

FIG. 7 is a side elevation, partly broken away, of a cartridge similar to that shown in FIGS. 1, 2 and 4, but on a larger scale, and illustrating a piston inserted in the open end of the cartridge and also showing fragmentarily a portion of a plunger rod of the ejector holder adapted to engage the piston of the cartridge.

DETAILED DESCRIPTION OF THE PREFERRED EMBODIMENT

Figure 8:
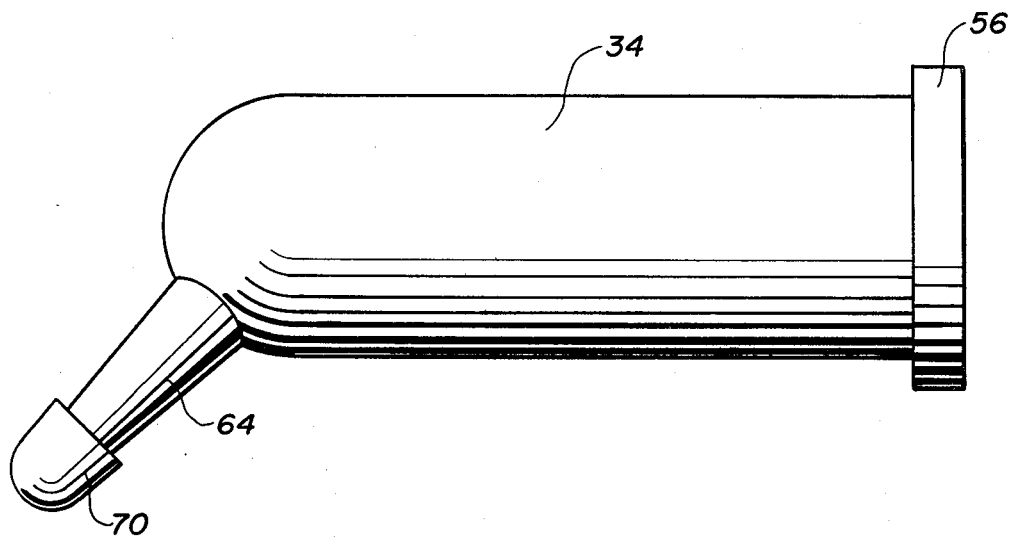
FIG. 8 is a side elevation of a cartridge similar to FIG. 7, but further including a cap for the discharge nipple of the cartridge body.
Figure 9:
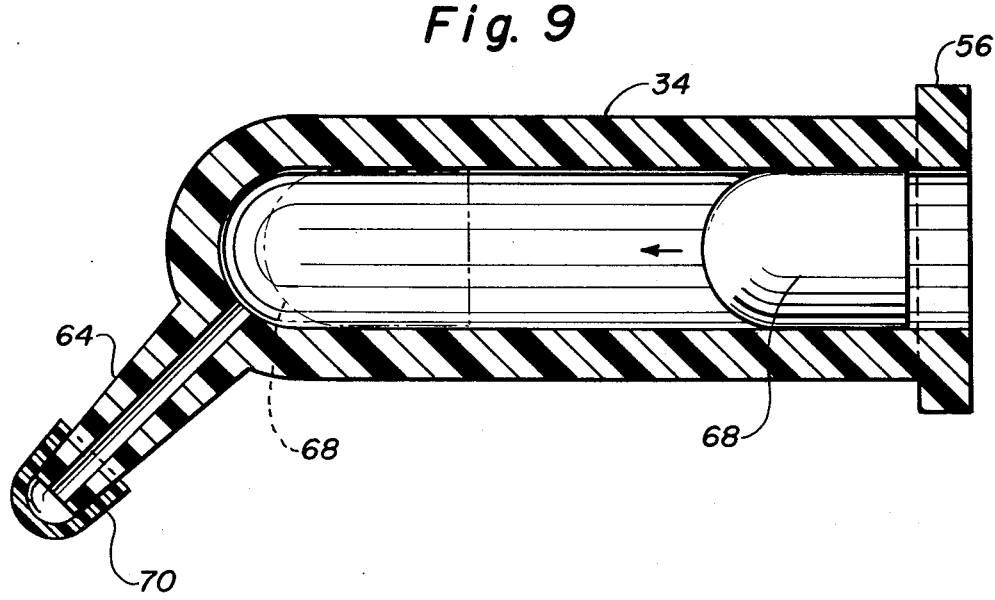
FIG. 9 is a vertical section of the cartridge shown in FIG. 8.

Referring to FIG. 1, there is shown therein an ejector holder of a type especially designed to hold in operative position a cartridge embodying the principles of the present invention. The holder is the subject matter of a companion continuation-in-part application and comprises a barrel 10 having a interior bore 12 extending from the rearward end 14 of the barrel toward the forward end 16 thereof for purposes of receiving a plunger 18 of the same diameter as that of the interior bore 12 for the major portion of the length of the plunger, the forward end of the plunger having a smaller diameter extension 20.

The rearward end 14 of the barrel 10 extends through and is fixed to a handle member 22 with which the barrel 10 is perpendicular. Pivotally connected to the handle 22 is an operating lever 24, the upper end of which is pivotally connected to the upper end of handle 22 by a pivot pin 26. The upper end 28 of operating lever 24 is offset laterally to facilitate operation of the lever 24 with respect to the outer end of plunger 18 which terminates in a button 30 engageable by the inner surface 32 of operating lever 24.

From FIGS. 1-4, it will be seen that the forward end 16 of the barrel 10 is tapered and is provided with a longitudinally extending opening comprising compartment 32 which extends rearwardly from the terminal end of the forward end 16 toward the interior bore 12. The lower surface of compartment 32, as viewed in FIG. 3, is semi-cylindrical and is complementary to the elongated body of cartridge 34 so as to receive and seat the same, as shown in FIGS. 1, 2 and 4. However, the sidewalls 36 and 38 of compartment 32 extend upwardly from the semi-cylindrical bottom surface shown in FIG. 3 and are parallel to each other for a limited distance and the upper edges 40 and 42 extend toward each other a limited distance. Said uppermost portions of sidewalls 36 and 38 also have limited flexibility, whereby the distance between the upper edges 40 and 42 of said sidewalls is slightly less than the diameter of the cartridge 34, whereby there is a snap-acting retaining function provided by said sidewalls and the upper edges 40 and 42 with respect to the cartridge 34 when the latter is inserted in the compartment 32.

The forward end 16 of the barrel 10 also has a cutaway portion 44 extending longitudinally rearward to form a shoulder 46, which determines the inner end of the cutaway portion. Due to the fact that the forward end 16 is tapered and the barrel 10 otherwise is circular, said cutaway arrangement provides flat surfaces 48 and 50. Also, as best shown in FIG. 3, the sidewalls of the compartment 32, at the inner ends thereof, have lateral recesses 52 and 54 which are spaced apart a greater distance than the diameter of the annular exterior flange 56 in order to permit the insertion of the flange into compartment 32 which, following radial insertion movement thereof into the compartment, the cartridge may be moved axially forward for disposition of the flange 56 in an undercut seat 58, which is clearly shown in FIGS. 3-5. Said seat, in conjunction with the portion of the compartment 32 extending forwardly therefrom, provides a firm means for supporting a cartridge 34, which is retained seated in said compartment, especially by means of the snap-fitting arrangement provided by the upper edges 40 and 42 of the sidewalls 36 and 38, as described hereinabove.

Without restriction thereto, the preferred material from which the barrel 10, handle member 22 and operating lever 24 are formed is a suitable rigid plastic material in order that these elements may be formed readily and accurately by molding from raw plastic material; obviously, the coiled spring 60 is formed from spring wire for purposes of retracting the plunger 18 when the operating lever 24 is released, following an ejection of material from the cartridge 34.

The cartridge 34 which comprises the subject of the instant application is also preferably formed by molding from appropriate rigid synthetic resin or plastic material by means of a suitable mold. The intermediate body portion of the capsule 34 is of uniform interior and exterior diameter and extends from annular flange 56 adjacent the open end of the cartridge to the opposite closed end 62. The body portion is cylindrical, whereas the closed end 62 is hemi-spherical but is provided with an angularly extending discharge nipple 64, the opening of which is preferably a very fine dimension of small diameter. To effect ejection of material from the cartridge 34, such as dental filling material, cement, or other viscous dental material and the like, for example, the cartridge 34 includes a piston 66, which is very closely complementary in diameter to the interior of the cartridge 34, and the inner end 68 thereof also is hemispherical and complementary to the interior of the closed end 62 of the cartridge. Without restriction thereto, the outer end of the piston may be flat for engagement, for example, with the extension 20, shown fragmentarily in FIG. 7, when the plunger 18 is moved forwardly by actuation of the operating lever 24.

Removal of the capsule 34 from the compartment 32 is accomplished readily by snapping the cartridge outwardly beyond the somewhat flexible upper edges 40 and 42 of the compartment after the contents within the cartridge have been discharged or exhausted, as required.

From the foregoing, it will be seen that the ejector holder is especially adapted to receive the particular type of cartridge to be used therewith, which is the subject of the instant application. The ejector is of very simple, highly effective design, to permit sure and quick mounting of the cartridge within the compartment in the forward end of the barrel of the holder and, with equal facility, removal of the cartridge therefrom is readily achieved.

The cartridge comprising the invention not only is capable of serving as a receptacle for material to be discharged when filled, for example, from a storage supply, but, even more importantly, the cartridge can be filled at a factory with predetermined quantities of material, by automatic machinery, and sealed therein by application of the piston 66, which, under the circumstance, serves as a closure for the cartridge. The above-described design particularly facilitates such operations. Further, during filling, air in the cartridge in advance of the material can be discharged through the nipple 64 until filled and then the open end of the nipple may suitably and inexpensively be closed by suitable seal means, such as a small piece of sheet material having pressure-sensitive cement on one side and fold said piece across the nipple in any suitable manner.

In accordance with the invention, a further improved feature for the cartridge comprises providing a preferably cup-shaped cap 70 which is suitably shaped either to frictionally engage the tip portion of the nipple 64, or either the cap or nipple, or both, may have appropriate threads formed therein or thereon to secure the cap releasably upon the tip of the nipple in sealed manner.

Moreover, the cap 70 serves an important additional possible feature in that, in addition to sealing the contents of the cartridge, in conjunction with the piston 66, the cap also may be color-coded for any a number of purposes such as to indicate the kind of material for specified purposes, weight or quantity of the material therein, setting time, and otherwise.

Also, the body of the cartridge as well as the cap 70 and piston 66 may all be molded from similar plastic material which is colored suitably to render the items opaque or otherwise impervious to the transmission of ambient light which, if the contents are subject to being set by such light, prevents premature setting thereof.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

I claim:

1. A miniature capsule-like cartridge adapted to be operated solely by being mounted upon an ejector-type holder and comprising in combination, a hollow elongated uniformly cylindrical body of predetermined length and uniform diameter interiorly and exteriorly and molded from rigid plastic material, one end of said body being open and formed at the extremity thereof with an annular relatively short circular exterior flange of limited width and adapted to be detachably mounted within a complementary seat in an ejector type holder, the opposite end of said body being closed by a hemispherical wall of substantially the same uniform thickness as said body, a discharge nipple of the same material as the body and molded integrally therewith and extending from said closed end of said body at an angle to the axis of said body to facilitate directing discharge from the cartridge to the interior of an oral cavity, a piston having sidewalls closely complementary to the inner walls of said body and inserted into the open end thereof to form a combination closure and ejecting means for material when contained in said cartridge, the inner end of said piston being hemispherical and complementary in shape to the interior surface of the closed end of said body to effect ejection of substantially the entire contents of said cartridge when said piston is fully inserted into said body of the cartridge, sealing means comprising a cup-shaped cap removably connected to the outer end of the discharge nipple on said body to close said outer end of the nipple to seal the contents of the cartridge against ingress of ambient atmosphere and/or any surrounding contaminating matter, and said cap being color-coded to indicate desired properties of the contents of the cartridge.

2. The cartridge according to claim 1 further characterized by said body and piston being formed from plastic material suitably colored to render the same impervious to the transmission of ambient light, thereby rendering the cartridge adapted to contain light-curable material and the like in a manner to prevent premature curing of such material while stored in such cartridge.

* * * * *

REEXAMINATION CERTIFICATE (1880th)
United States Patent [19]
Dougherty

[11] B1 4,391,590

[45] Certificate Issued Dec. 15, 1992

[54] CARTRIDGE FOR VISCOUS MATERIAL

[75] Inventor: Emery W. Dougherty, York, Pa.

[73] Assignee: Dentsply Research & Development Corp., Milford, Del.

Reexamination Request:
No. 90/002,417, Aug. 26, 1991
No. 90/002,144, Sep. 21, 1990

Reexamination Certificate for:
Patent No.: 4,391,590
Issued: Jul. 5, 1983
Appl. No.: 344,255
Filed: Jan. 29, 1982

[51] Int. Cl.$^5$ ............................................. A61C 5/04
[52] U.S. Cl. ..................................... 433/90; D24/113
[58] Field of Search ........................... 433/90, 89, 80; 222/386

[56] References Cited

U.S. PATENT DOCUMENTS

| | | | |
|---|---|---|---|
| 1,188,417 | 6/1916 | Dalby | |
| 2,050,246 | 8/1936 | Colvin | 299/90 |
| 2,505,028 | 4/1950 | Boeger | 128/215 |
| 2,847,009 | 8/1958 | Blease | 128/222 |
| 3,164,303 | 1/1965 | Trautmann | 222/190 |
| 3,212,685 | 8/1965 | Swan | 222/386 |
| 3,464,412 | 9/1969 | Schwartz | 128/218 |
| 3,489,147 | 1/1970 | Shaw | 128/218 |
| 3,581,399 | 6/1971 | Dragan | 32/60 |
| 3,595,439 | 7/1971 | Newby | 222/60 |
| 3,815,878 | 6/1974 | Baskas | 259/37 |
| 3,900,954 | 8/1975 | Dragan | 32/60 |
| 3,907,106 | 9/1975 | Purrmann | 206/219 |
| 3,955,719 | 5/1976 | Fheulpin | 222/386 |
| 3,998,224 | 12/1976 | Chiquiar-Arias | 128/218 R |

FOREIGN PATENT DOCUMENTS

298292 10/1928 United Kingdom .

OTHER PUBLICATIONS

Dental Products Report (DPR) Oct. 1981.
Lactona Catalogue Prior to 1975.
Milford News Prior to 1930.
Espe-Applic-System Publication 1979–1980.
Dental Products Report (DPR) Jun. 1970.
Dental Survey Jun. 1970.
Centrix Brochure Dec. 1970.
3M Technical Information Jul. 1974.
SS White Composite Syringe Publication 1979.
Cavitron Catalogue 1972.
Dent-O-Lux Prior to 1970.
Espe Publication for Capsule Applicator Circa 1979–1980 Ex. 5B.
Espe Nimeticap Publication 1977 Ex. 5C.
Espe Ketac-Fil Publication 1979–1980 Ex. 5&5A.
Cavitron Catalogue c. 1972 Ex. 10.
Dental Products Report Jun. 1970 Ex. 7.
3M Technical Information Jul. 1974 Ex. 6.
Dental Products Report (Centrix Black Tubes) Oct. 1981 Ex. 1.
Milford News, Prior to 1930.
Dent-O-Lux Capsule Prior to 1970.

*Primary Examiner*—Cary E. O'Connor

[57] ABSTRACT

A capsule-like cartridge comprising a cylindrical body of uniform diameter open at one end and provided with an annular flange surrounding the open end, the other end being closed by an integral hemi-spherical end of the same radius as said body and provided with an angularly extending discharge nipple communicating with the interior of the hemi-spherical end and body. After the body is loaded with a precisely measured quantity of material, the open end is closed by a plug slidably movable along said body when one end is engaged by a plunger of no greater diameter than said plug and the opposite end being complementary in shape to the hemi-spherical end of the body, whereby the plunger is capable of discharging the entire measured amount of material in the body except the scintilla thereof lodged in the nipple. The body and plug are molded from opaque material impervious to the passage of light and the tip of the nipple is closed by a cap which may be color-coded to indicate various facts as kind of material, weight or quantity, or otherwise.

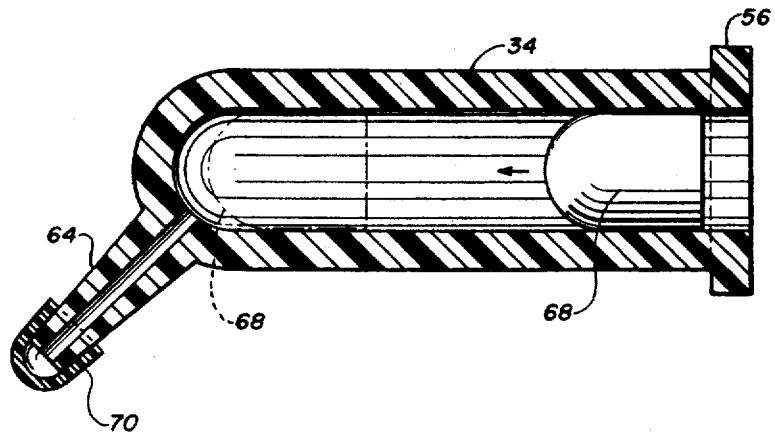

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1 and 2 is confirmed.

* * * * *